United States Patent [19]

Dunnigan

[11] 4,051,190

[45] Sept. 27, 1977

[54] MANUFACTURE OF 3-ARYLPROPYL CHLORIDE

[75] Inventor: Daniel Ambrose Dunnigan, Winthrop Harbor, Ill.

[73] Assignee: Abbott Laboratories, North Chicago, Ill.

[21] Appl. No.: 653,809

[22] Filed: Jan. 30, 1976

[51] Int. Cl.$^2$ .............................................. C07C 25/14
[52] U.S. Cl. ........................ 260/651 R; 260/651 HA
[58] Field of Search ..................... 260/651 R, 651 HA

[56] References Cited
PUBLICATIONS

Migrdichian, Organic Synthesis, vol. 1, pp. 176–177 (1956).

*Primary Examiner*—C. Davis
*Attorney, Agent, or Firm*—Paul D. Burgauer; Robert L. Niblack

[57] ABSTRACT

A two-step preparation of 3-arylpropyl chloride from the corresponding 2-chloropropiophenone by hydrogenation using two specific catalysts in series.

9 Claims, No Drawings

MANUFACTURE OF 3-ARYLPROPYL CHLORIDE

DETAILED DESCRIPTION OF THE INVENTION

Compounds of the formula

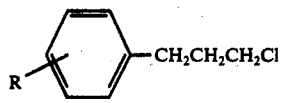
I wherein R represents alkyl, hydrogen or halogen, have been used widely in the synthesis of physiologically active compounds such as, for instance, required to produce the 8-position substituent for the compound of U.S. Pat. No. 3,878,219. The most economical way for making the above compounds is the use of the corresponding 2-chloropropiophenone

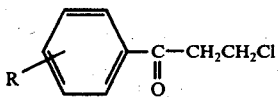
II which, through hydrogenation of the keto group should yield I. However, ordinary methods have always led to failure because the keto group activates the β-position causing the chlorine to be lost in standard catalytic hydrogenation procedures.

It is therefore an object of this invention to provide an economical method for making I; it is a more particular object to provide a method for preparing I from II; it is an even more specific object of this invention to provide a catalytic hydrogenation which leads from II to I.

These and other objects are accomplished by providing a two-step process for the preparation of an arylpropyl chloride of the formula

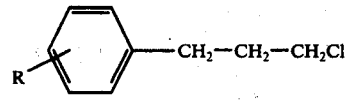

wherein R is hydrogen, loweralkyl or halogen, consisting essentially in hydrogenating a solution of an arylpropiophenone of the formula

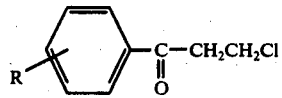

in an inert solvent in the presence of a catalyst containing metallic ruthenium on a suitable inert support until an equimolar amount of gaseous hydrogen is used and, after removing said catalyst from said solution, hydrogenating the mixture in the presence of a mineral acid and a catalyst containing metallic palladium on a suitable solid support until one equimolar amount of the gaseous hydrogen has been used.

The "inert support", referred to above, is intended to define the customary support materials used for metallic catalysts, e.g. bentonite, kieselguhr, carbon, silica gel, alumina, etc. Ordinarily, such a support contains between 2 ½ and 10 percent by weight of the metallic catalyst. "Inert solvent" refers to those liquids that provide sufficient solubility for the arylpropiophenone to dissolve that material and to be non-reactive toward all the other components present in the reaction mixture. The term "equimolar amount" will readily be understood by those skilled in the art to refer to a molar equivalent of hydrogen in each step of the above reaction.

As mentioned above, the current process is carried out in two steps, each step requiring its own metallic catalyst. Such a procedure provides for the retention of the reactive chlorine substitutent at the alkyl terminus of I, which otherwise is always lost during a catalytic hydrogenation involving the chloropropyl group. This phenonmenon, the loss of the terminal chlorine group is unique in compounds of the above nature, since those compounds where the terminal chlorine is separated from the aryl group by more or less hydrocarbon groups are devoid of the additional and undesirable reaction by which said chlorine is replaced hydrogen as well.

The current invention is therefore specifically required for the treatment of arylphenones wherein the other valance of the carbonyl group is represented by the 2-chloroethyl radical. If that group was, for instance, the chloropropyl group, the terminal chlorine would not be affected by an ordinary catalytic reduction and the carbonyl group could be reduced to a methylene group by direct use of metallic palladium as the catalyst or by a mixed catalyst containing palladium and ruthenium. Such catalysts have been known and have been used in the past, but they are totally unsuitable in the above procedure due to their adverse effect on the chlorine function.

Ordinarily, both steps of the above reaction can be carried out in the presence of 1 to 10 percent by weight of the metallic catalyst per se. Using higher amounts within this range, the catalytic procedure is somewhat more accelerated, but no great advantage is seen in using catalyst amounts greater than about 5 percent by weight based on the use of metal catalyst versus the compound of formula II.

Both of the above steps can also be carried out within a wide range of temperatures and pressures. Where the solvent used permits, temperatures from 10° to 100° C can be used, with the higher temperatures providing a somewhat faster uptake of hydrogen. Hydrogen pressures of 1-100 atm. can be used, but it is a particular advantage of the present invention that hydrogenation proceeds satisfactorily at pressures below 3 atm., permitting the use of so-called "low pressure" equipment such as an ordinary still, a Parr shaker or an ordinary round-bottom flask. As well known to those skilled in the art, higher temperatures are sometimes desired to accelerate the reaction, but for ordinary purposes, operating between room temperature and about 50° C and at pressures below 3 atm., satisfactory results in quality and quantity of end-product are obtained.

In addition to the above advantages of the present method, the new two-step reaction is also very practical for reasons that the reaction product of the first step of the reaction does not have to be isolated; it is sufficient to filter off the catalyst used in the first step and to use the filtrate directly for the second hydrogenation by the addition of the catalyst described for that step.

In order to illustrate the process of the current invention, reference is made to the following Example which, however, is not intended to limit the invention in any respect.

EXAMPLE

To 18.7 g. of 4-fluorophenyl-3'-chloropropiophenone in 250 ml of 80% aqueous methanol is added 9 g. of 5% ruthenium-on-carbon, and the mixture is hydrogenated in a closed vessel under 3 atm. of hydrogen pressure until 0.1 mole of hydrogen is consumed. The catalyst is then filtered off and 25 ml of concentrated hydrochloric acid and 4 g. of 5% palladium-on-carbon is added. This mixture is again hydrogenated under 3 atm. of pressure until 0.1 mole of hydrogen is consumed. The catalyst is then filtered off; the methanol is distilled off and the aqueous residue extracted with ether. Upon drying the ether solution over sodium sulfate and distilling the residue, 4- fluorophenylpropylchloride is obtained in a yield of 11.6 g. (67% of theory), showing a boiling point of 95°-7° C (11mm) at a purity of 99% established by gas-liquid chromatography.

When in the above Example the same procedure is followed with equimolar amounts but using chloropropiophenone without substituent in the aryl group as the starting material, the corresponding phenylpropylchloride is obtained in a yield of about 72% of theory. However, when the above catalyst is replaced by palladium, platinum or a ruthenium/palladium mixture in the first step, the desired product is not obtained.

It is particularly advantageous to use, as a solvent in the above reaction, an aqueous mixture of a low boiling alcohol such as methanol, ethanol, propanol or isopropanol. A mixture thereof with 20-50% by volume of water is particularly well suited to facilitate the workup of the obtained arylpropyl chloride: In the presence of water, there is no need to azeotrope the resulting filtrate after removal of the catalyst. However, it is to be understood that any other alcohol as well as other inert solvents, such as tetrahydrofuran, dioxane, diethyl ether or mixtures of these materials may be used in place of a low boiling alcohol.

While the above procedure calls for the use of hydrochloric acid for the second step of the hydrogenation, it will be well recognized by those skilled in the art that other acids may be used, for instance sulfuric acid or alkyl sulfonates which, for the purpose of this invention, are meant to be included in the term "mineral acids". However, the use of hydrochloric acid is often preferred, since it does not introduce any chemical components that are not already present in the reaction mixture. For reasons of minimizing the volume with which the workup has to be carried out, the addition of a small amount of concentrated mineral acid is best suited. Where volume is of no object, dilute forms of hydrochloric or sulfuric acids can be used without detriment.

What is claimed is:

1. A two-step process for the preparation of an arylpropyl chloride of the formula

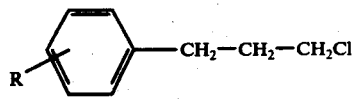

wherein R is hydrogen, loweralkyl or halogen, consisting essentially in hydrogenating a solution of an arylpropiophenone of the formula

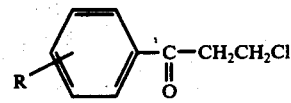

in an inert solvent in the presence of a catalyst containing metallic ruthenium on a suitable inert support at a temperature between 10° C and 100° C and at a hydrogen pressure between 1 and 100 atm. until an equimolar amount of gaseous hydrogen is used and, after removing said catalyst from said solution, hydrogenating the mixture in the presence of a mineral acid and a catalyst containing metallic palladium on a suitable solid support at a temperature between 10° C and 100° C and at a hydrogen pressure between 1 and 100 atm. until a second equimolar amount of the gaseous hydrogen has been used.

2. The process of claim 1 wherein said hydrogenations are carried out at a temperature between room temperature and 50° C.

3. The process of claim 1 wherein said arylpropiophenone is the p-fluoroaryl-3-chloropropylphenone.

4. The process of claim 1 wherein said inert solvent is methanol.

5. The process of claim 4 wherein said methanol contains between 20 and 50% by volume of water.

6. The process of claim 1 wherein said hydrogenations are carried out at pressures of between 1 and 3 atm.

7. The process of claim 1 wherein said ruthenium and said palladium are supported on carbon.

8. The process of claim 7 wherein said carbon carries 5% by weight of said catalyst.

9. The process of claim 1 wherein said mineral acid is hydrochloric acid.

* * * * *